(12) United States Patent
Styrc

(10) Patent No.: US 8,623,072 B2
(45) Date of Patent: Jan. 7, 2014

(54) TUBULAR PROSTHESIS AND ASSOCIATED KIT

(75) Inventor: Witold Styrc, Kopstal (BE)

(73) Assignee: Laboratoires Perouse, Ivry le Temple (FR)

( * ) Notice: Subject to any disclaimer, the term of this patent is extended or adjusted under 35 U.S.C. 154(b) by 256 days.

(21) Appl. No.: 12/213,545

(22) Filed: Jun. 20, 2008

(65) Prior Publication Data

US 2008/0319552 A1 Dec. 25, 2008

(30) Foreign Application Priority Data

Jun. 20, 2007 (FR) ...................... 07 55892

(51) Int. Cl.
*A61F 2/06* (2013.01)
(52) U.S. Cl.
USPC ......... 623/1.36; 623/1.11; 623/23.7; 606/151
(58) Field of Classification Search
USPC ............... 623/1.23, 1.25, 1.36, 23.7
See application file for complete search history.

(56) References Cited

U.S. PATENT DOCUMENTS 6,451,048 B1 * 9/2002 Berg et al. .................. 623/1.13

2005/0277947 A1 * 12/2005 Ziegler ..................... 606/113
2007/0043432 A1 * 2/2007 Perouse ..................... 623/1.36
2007/0198097 A1 8/2007 Zegdi

FOREIGN PATENT DOCUMENTS

| FR | 2 865 926 | 8/2005 |
|---|---|---|
| WO | 2005/070343 | 8/2005 |
| WO | 2006/047573 | 5/2006 |

OTHER PUBLICATIONS

French Search Report issued Jan. 25, 2008 issued in French Application No. 0755892.

* cited by examiner

*Primary Examiner* — David H Willse
*Assistant Examiner* — Tiffany Shipmon
(74) *Attorney, Agent, or Firm* — Wenderoth, Lind & Ponack, L.L.P.

(57) ABSTRACT

A tubular prosthesis is radially deformable and includes a lattice that is deformable between a retracted state of small diameter and an expanded state of larger diameter. The prosthesis includes at least two outer hooks delimiting between them a clamp for engaging in an outer tissue. The two hooks are carried by the lattice and can be moved between a spaced-apart position in which the clamp is open and a closer-together position in which the clamp is closed. The prosthesis includes a guiding member for moving at least one of the hooks during deformation of the prosthesis. The guiding member delimits a guide passage in which at least one of the hooks is engaged.

20 Claims, 10 Drawing Sheets

TUBULAR PROSTHESIS AND ASSOCIATED KIT

TECHNICAL FIELD

The present invention relates to a radially deformable tubular prosthesis, of the type comprising a tubular body deformable between a retracted state of small diameter and an expanded state of larger diameter. The prosthesis includes at least two outer hooks delimiting between them a clamp for engaging in an outer tissue, the two hooks being carried by the body and moveable between a spaced-apart position in which the clamp is open and a closer-together position in which the clamp is closed.

BACKGROUND OF THE INVENTION

For different types of treatment, putting a tubular prosthesis in place inside a blood vessel, whether a vein or an artery, is known. Such tubular prostheses are generally designated by the term "stent". WO-A-2005/079705 describes such a prosthesis. The prosthesis is introduced inside the vessel while the prosthesis is in the retracted state. Then, to put it in place, the prosthesis is expanded so as to be applied against the inner surface of the vessel. This expansion occurs either automatically because of the resilience of the prosthesis lattice, or by inflating a small inner balloon, causing plastic deformation of the material making up the lattice.

To avoid subsequent displacement of the prosthesis, the end of the metal lattice has pairs of hooks each forming an engagement clamp to immobilize the prosthesis axially in the vessel.

Each clamp is thus delimited by two hooks carried by the lattice that can move between a spaced-apart position in which the clamp is open and a closer-together position in which the clamp is closed. Each hook is threadlike and has one end fixed to the lattice. The other end of the hook is free and forms an endpiece for engaging in the tissue delimiting the blood vessel.

The two fixing ends of each clamp are carried by the same mesh of the lattice. The hooks are moved from their spaced-apart position to their closer-together position by moving the fixing end thereof when the mesh carrying the clamp expands. The mesh is first held in a retracted state during expansion of the entire lattice, then released to close the clamp.

However, the lattice does not deform uniformly, in particular depending on the morphology of the blood vessel in which it is implanted. The free ends of the hooks forming the same clamp can therefore be separated from each other in particular after expansion of the lattice. This impairs the robustness of the fixture of the lattice in the tissue delimiting the vessel.

SUMMARY OF THE INVENTION

The object of the invention is to propose a tubular prosthesis that allows more reliable engagement of the lattice of the tubular prosthesis in the vessel.

Accordingly, the invention relates to a tubular prosthesis of the above-mentioned type, in which the prosthesis comprises a member for guiding the movement of at least one of the hooks during deformation of the prosthesis. The guiding member delimits a guide passage in which at least one of the hooks is engaged.

According to particular embodiments, the tubular prosthesis comprises one or more of the following characteristics:

- the hooks comprise a guiding hook and a guided hook, the guiding member being formed on the guiding hook, the guide passage receiving the guided hook,
- the guiding member is formed by twisting the guiding hook on itself,
- twisting is performed over at least one turn,
- each hook is connected to the body from a connection end, and the hooks of the same clamp can move in relation to one another during deformation of the prosthesis,
- the body comprises a resilient ring encircling the body, the ring being connected to the body and being deformed with the body between a retracted state and an expanded state, the ring carrying the two hooks and moving them between their spaced-apart position and their closer-together position during deformation thereof,
- the body comprises a lattice that can be deformed between the retracted state and the expanded state and which comprises interlaced threads that form meshes in the form of deformable quadrilaterals, and each hook is connected to the lattice in a corner of the quadrilateral,
- each hook is fixed to the lattice at its connection end,
- each hook is extended at its connection end by a strand twisted round the lattice, and/or
- the tubular body comprises a fabric that is deformable between the retracted state and the expanded state, the two hooks being fixed on the fabric in such a way that deployment of the fabric moves them between their spaced-apart position and their closer-together position.

The invention also relates to a blood vessel treatment kit, which comprises:
- a prosthesis as described above;
- means for retaining the lattice retracted in the region of the or each clamp; and
- a tube for delivery of the lattice delimiting a conduit for confinement of the prosthesis in its retracted state.

According to a particular embodiment, the confinement conduit of the delivery tube comprises longitudinal channels for receiving the hooks.

BRIEF DESCRIPTION OF THE DRAWINGS

The invention will be better understood upon reading the description that follows, given solely as an example and with reference to the drawings, in which.

DESCRIPTION OF PREFERRED EMBODIMENTS

Figure 1:
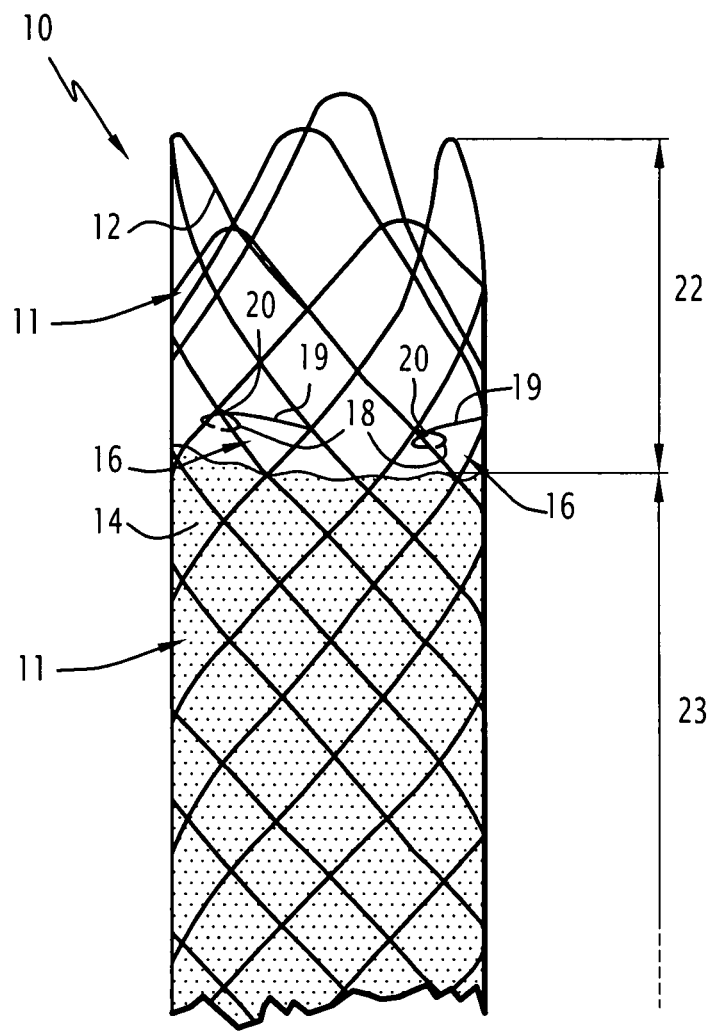
FIG. 1 is a perspective view of a tubular prosthesis in the expanded state.

The tubular prosthesis 10 illustrated in FIG. 1 is designed to be put in place in a blood vessel. It comprises a tubular body 11 comprising a lattice 12 embedded, over most of the length of the prosthesis, in a film 14 of the body 11. The prosthesis 10 also comprises, in the vicinity of one of its ends, three clamps 16 spaced regularly at angles on its periphery.

Each clamp 16 is made up of two hooks 18, 19 carried by the metal lattice 12. These hooks 18, 19 can be moved in relation to each other between a spaced-apart position in which the clamp is open and a closer-together position in which the clamp is closed. The clamp further comprises a guiding member 20 carried on one of the hooks 18, 19 (see FIGS. 2 and 3). The hook 18, 19 carrying the member 20 is a guiding hook 18 delimiting a guide passage 21 in which the other hook, a guided hook 19, is engaged.

In the example illustrated, the clamps 16 are provided on an end portion 22 of the prosthesis with no film 14, the lattice 12 therefore not being covered in this region. However, in the main portion 23 of the prosthesis, the lattice 12 is embedded in the film 14. In a variant, the clamps 16 are provided over the entire length of the prosthesis, in particular where the prosthesis has no film.

The lattice 12 consists of biocompatible stainless steel. It is produced for example by weaving or knitting a thread, axial deployment of a tube, or by any other appropriate technique.

In the embodiment illustrated in FIG. 1, the lattice 12 consists of two bundles of threads wound in a helix in opposite directions, the threads in the same bundle extending generally parallel to one other and transverse to the threads in the bundle of threads wound in the opposite direction. The threads of the two bundles wound in opposite directions cross each other alternately above and beneath to form meshes.

The lattice 12 is preferably elastically deformable by radial expansion, between a retracted state of small diameter and an expanded state of larger diameter.

Figure 5:
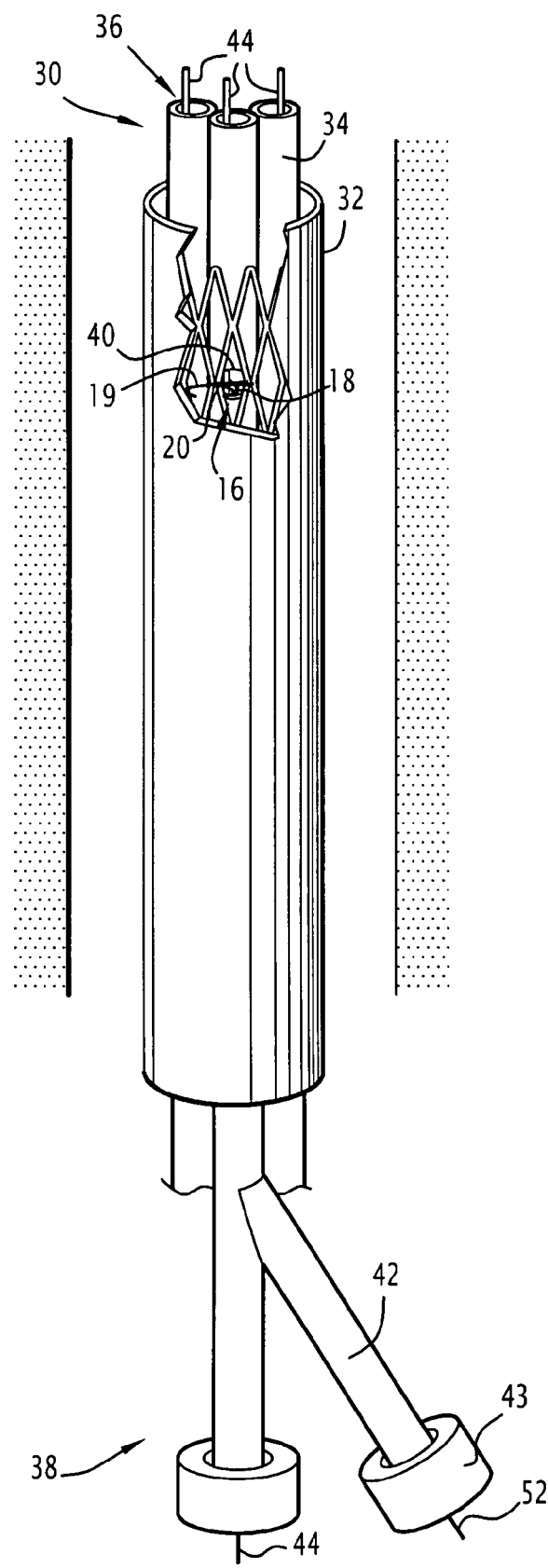
FIG. 5 is a perspective view of the prosthesis during implantation in the retracted state of FIG. 4.

In its expanded state, illustrated in FIG. 1, the meshes of the lattice form diamonds generally elongated in the circumferential direction. Conversely, and as illustrated in FIG. 5, in the retracted state of the prosthesis, the meshes form diamonds elongated parallel to the axis of the prosthesis.

In a variant, the prosthesis is plastically deformable. In other words, the body 11 and the lattice 12 have a first stable form of small diameter and a second stable form of larger diameter.

Over the main portion 23, the lattice 12 is entirely embedded in the film 14. This film is formed of an expandable material that is impermeable with respect to the liquids that fill the meshes.

This material is sufficiently expandable for the film 14 to follow the deformation of the lattice 12 from its retracted state to its expanded state without tearing or coming loose, despite the deformation of the meshes and of the lattice. Appropriate materials are a biocompatible elastomer, which may be natural, or synthetic rubber or a biocompatible polymer such as polyurethane.

Coating of the lattice 12 by the film 14 is obtained for example by a coextrusion or steeping technique, after degreasing the metal and treating it with a primary adhesion substance.

Figure 2:
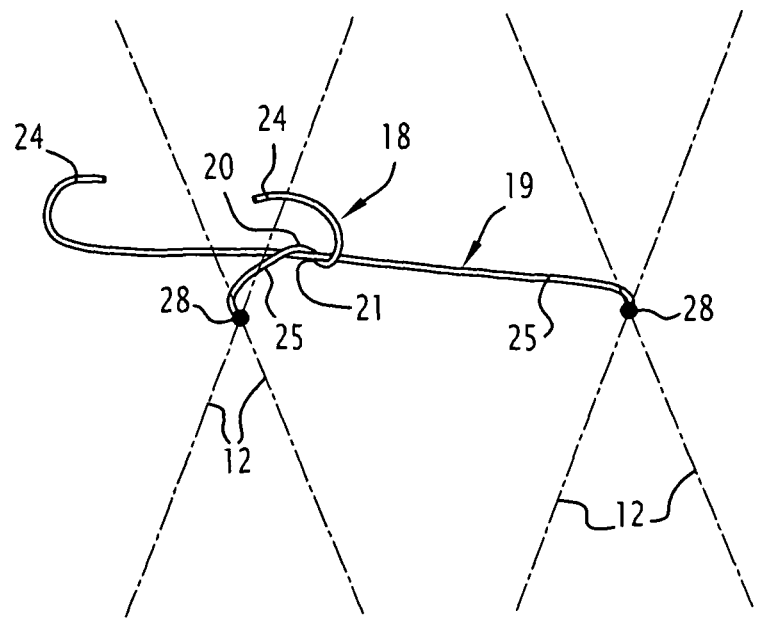
FIG. 2 is a perspective view from below on a larger scale of the prosthesis in the expanded state in a region comprising a clamp in an open position.
Figure 3:
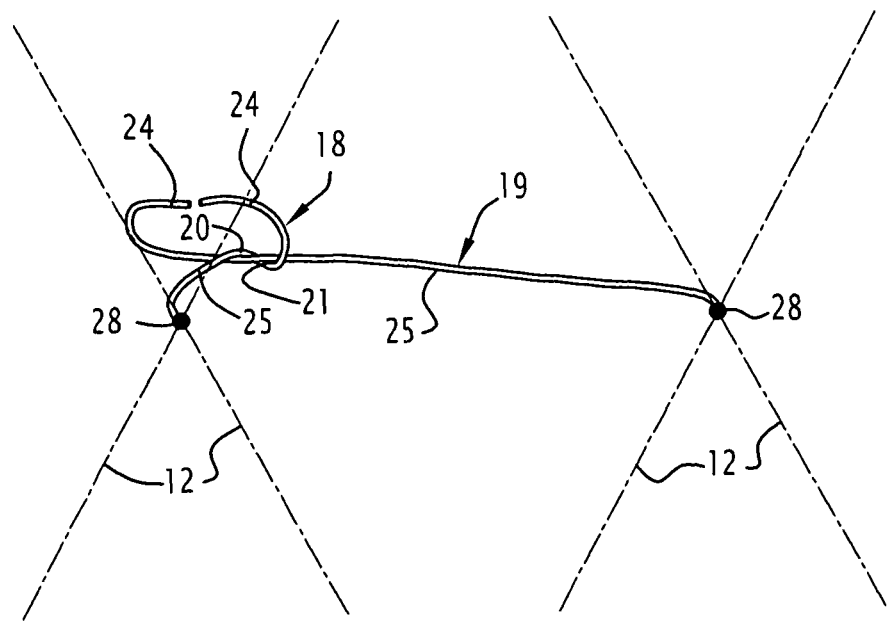
FIG. 3 is a similar view to FIG. 2, the clamp being in a closed position.
Figure 4:
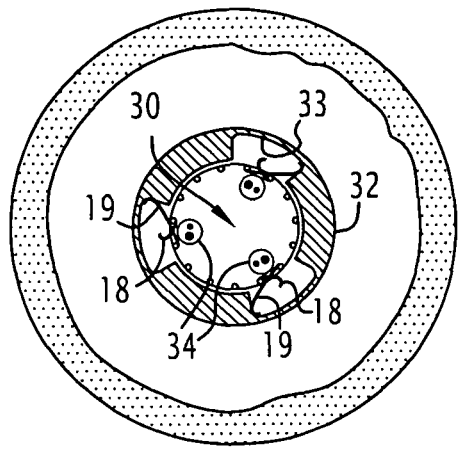
FIG. 4 is a cross-section of the prosthesis in the retracted state.

As illustrated in FIGS. 2 and 3, each hook 18, 19 is formed of a threadlike metal element, a free end of which is curved outwards to form an endpiece 24. The hooks 18, 19 overlap to form the clamp 16 between the facing endpieces 24. The endpieces 24 are alike.

Each hook 18, 19 comprises an arm 25 extended by the endpiece 24.

The arm 25 of the guided hook 19 consists of a rectilinear portion. However, the arm 25 of the guiding hook 18 comprises a loop forming the guiding member 20. The loop is produced by twisting the hook 18 upon itself over one, or any other suitable number of turns. The twisting is performed around the guided hook 19, which facilitates assembly of the clamps 16. Moreover, twisting is by plastic deformation, so that it is permanent.

The guiding member 20 formed by twisting is situated in the vicinity of the endpiece 24 of the guiding hook 18, in the extension of the endpiece 24.

The guided hook 19 can move along an axis of translation and two orthogonal axes of rotation in the passage 21 delimited by the guiding member 20. The mechanical stresses that could be exerted between the two hooks 18, 19 are thus minimized.

In a variant, the guiding member 20 is formed by twisting the hook 18 upon itself over more than one turn.

In another variant, the passage 21 is not delimited by a loop. It is for example delimited by a ring, or tube, or any other element with a form suitable for guiding the hook 19.

At its end opposite the endpiece 24, each arm 25 is fixed to the metal lattice 12 in opposite corners of a mesh as seen in FIGS. 2 and 3. The endpieces 24 project outwards in relation to the tubular portion delimited by the body 11 and the lattice 12, and their curved ends extend, at rest, in a plane transverse to the tubular prosthesis (in other words, perpendicular to the general axis thereof).

The diameter of the endpieces 24 of the hooks 18, 19 is between 0.1 and several millimeters. Preferably, the diameter of the endpieces 24 is smaller than the diameter of the passage 21.

The length of the arm 25 of the guided hook 19 is adapted to the diameter of the prosthesis 10. The length of the arm 25 of the guiding hook 18 is small and is smaller than that of the arm 25 of the guided hook 19 in such a way that the guiding member 20 is very close to the anchoring point 28 of the hook 18. In fact, the short length of the arm 25 of the guiding hook 18 provides rigidity to the arm 25 and thus increases guiding reliability.

The diameter of the guide passage 21 is greater than the diameter of the cross-section of the arm 25 of the hook 19.

The lengths of the arms 25 are such that, in the expanded state of the prosthesis illustrated in FIG. 1, the two endpieces 24 of the hooks 18, 19 are brought closer and together delimit a closed or practically closed loop.

Initially, and as illustrated in FIGS. 4, 5, 6, 7 and 8, the prosthesis is associated with a retaining device 30 for releasably retaining the clamps 16 in their open position.

Further, the prosthesis 10, the clamps 16 of which are held open, is received, as is known per se, in a delivery tube 32 inside which the prosthesis is confined, in the retracted state thereof.

Advantageously, the inner conduit of the tube 32 has canals 33 longitudinally for receiving the ends of the hooks 18, 19 projecting in relation to the generally tubular surface of the metal lattice.

Figure 6:
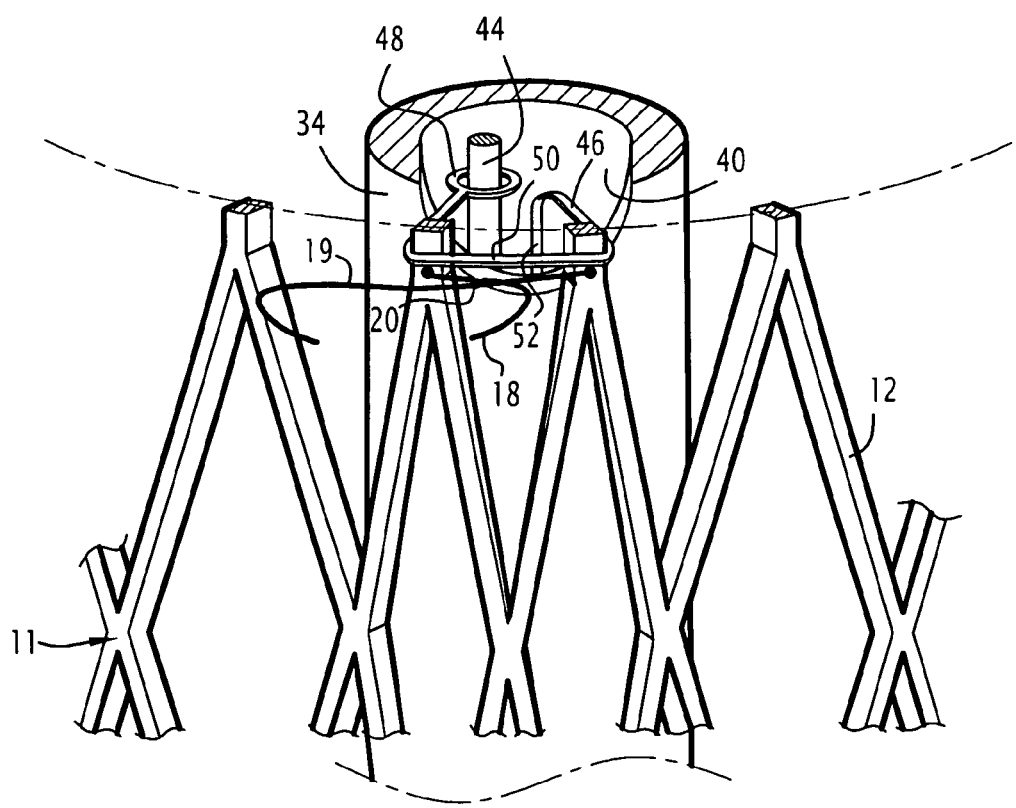
FIG. 6 is a view in section on a larger scale of the prosthesis in its retracted state in a region comprising a clamp in the open position.

As illustrated more precisely in FIGS. 5 and 6, each retaining device 30 for holding a clamp 16 open comprises a flexible tube 34 made for example of PEEK. This tube 34 extends longitudinally between a distal end 36 intended to be received in the blood vessel and a proximal end 38 intended to be accessible by the surgeon outside the patient's body. Therefore, the tube 34 has for example a length of one meter.

A retaining opening 40 is arranged laterally in the tube 34 generally facing the associated clamp 16. The tube 34 is further equipped, in the vicinity of its proximal end 38, with a hollow side branch 42 provided with a ring 43 for axially locking a sliding thread.

The releasable retaining retaining device 30 further comprises a retaining rod 44 engaged axially in the tube 34, and a retaining thread 46 encircling the mesh of the prosthesis carrying the clamp 16.

The retaining rod 44 extends from one end of the tube 34 to the other. It projects outside the tube at the proximal end 38. This rod 44 is moveable in the tube 34 between a retaining position (in which the rod is facing the opening 40) and a release position (in which the rod 44 is spaced-apart from the opening 40 and shifted towards the proximal end of the tube 34).

The retaining thread 46 comprises a single strand which has at one end a circlet 48, a tightening loop 50 and a control portion 52 which extends along the entire length of the tube 34 from the opening 40 to the branch 42 out of which it projects after having passed through the locking ring 43.

The end circlet 48 is formed by a closed loop of small diameter in which the rod 44 is engaged initially when the rod 44 is in its retaining position. The tightening loop 50 is formed by a portion of the strand, engaged so as to slide through two meshes of the lattice adjacent to the mesh carrying the clamp 16.

The tightening loop 50 passes through the opening 40 to join the circlet 48 at one end and the control portion 52 at its other end. The active length of the tightening loop 50 varies according to the traction applied to the control portion 52, in such a way that it controls the form (width) of the mesh carrying the clamp 16, as will be set out below.

Initially, before being put in place, the prosthesis is arranged in the delivery tube 32 and the control portions 52 of the retaining device 30 for retaining the clips are taut, so that the clamps are held open, as illustrated in FIGS. 5 and 6. In fact, in this position, the tightening loop 50 tightens the mesh carrying the clamp, so that the diamond defining the mesh is extended along the diagonal thereof parallel to the axis of the prosthesis.

Figure 7:
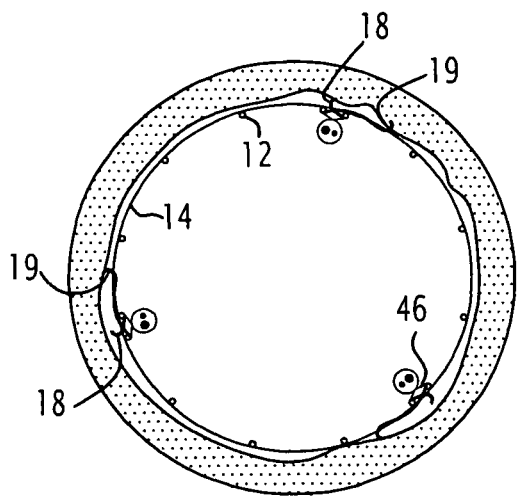
FIG. 7 is a similar view to that of FIG. 4 of the expanded prosthesis before engagement.
Figure 8:
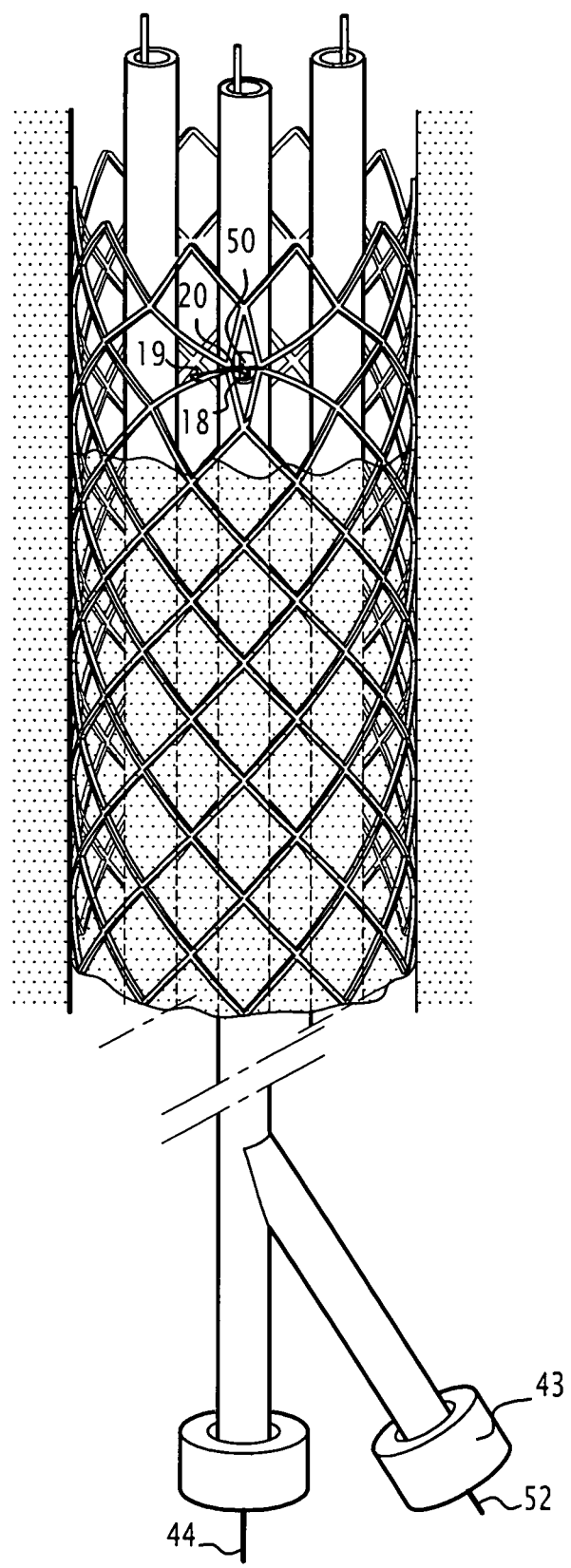
FIG. 8 is a perspective view of the expanded prosthesis before engagement.

To put the prosthesis 10 in place, the prosthesis 10 is introduced with the tube 32 as far as the insertion zone, and then the tube 32 is withdrawn thus releasing the prosthesis. The prosthesis 10 expands and is then laid flat against the inner surface of the blood vessel, as illustrated in FIGS. 7 and 8.

During this expansion, the meshes of the lattice of the prosthesis extend due to the resilience of the lattice along the peripheral diagonal of the prosthesis 10 thus allowing the diameter of the prosthesis to increase. Conversely, the meshes carrying a clamp remain contracted, as illustrated in FIG. 8 because of the tightening loop 50. Thus, the clamps 16 are laid against the surface of the blood vessel while the clamps 16 are still in the open position.

Figure 9:
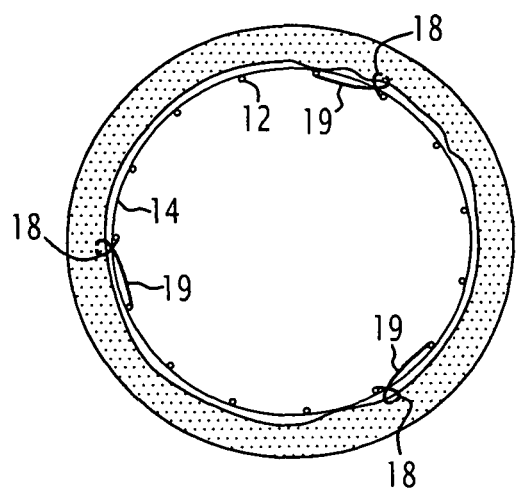
FIG. 9 is a view similar to FIG. 4 of the expanded and engaged prosthesis after removal of the clamp retaining members.
Figure 10:
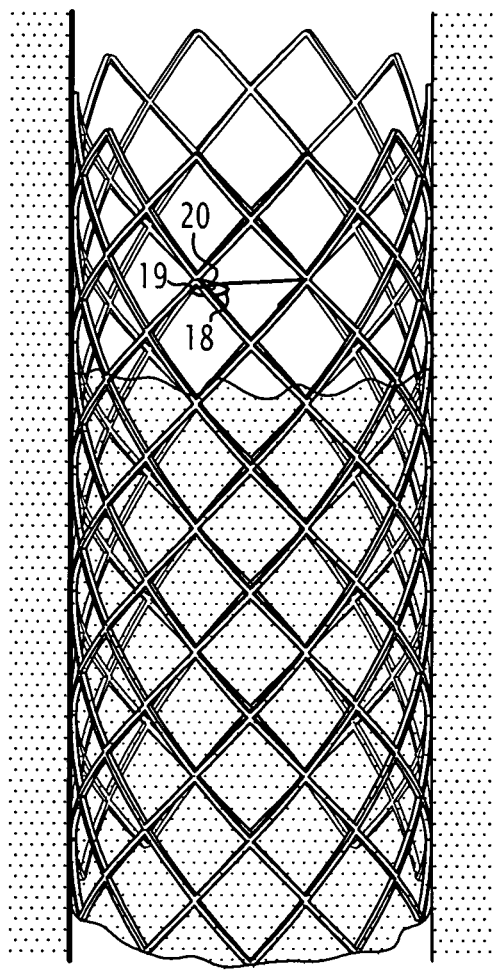
FIG. 10 is a perspective view of the expanded prosthesis after removal of the clamp retaining members.

By acting on the locking ring 43, the practioner then proceeds to release the retaining threads 46 to allow the elastic deformation of the meshes carrying the clamps 16, and the two opposite hooks 18, 19 therefore draw closer, causing each clamp 16 to close and the hooks 18, 19 to penetrate into the wall delimiting the blood vessel, as illustrated in FIGS. 9 and 10.

As the two hooks 18, 19 draw closer, the guided hook 19 slides in the guiding member 20. The guiding member 20 is situated in the vicinity of the endpiece 24 of the guiding hook 18, so the endpiece 24 of the guided hook 19 necessarily draws closer to that of the guiding hook 18 when the clamp 16 closes. This closure is therefore reliable whatever the deformation of the lattice 12. Thus, even if the deformation of the mesh carrying the clamp 16 is not uniform, the relative position of the endpieces 24 of the two hooks 18, 19 is substantially the same as during a uniform deformation of the mesh. In fact, in the closer-together position, the endpieces 24 are held in the vicinity of each other by the guiding member 20 and the clamping function of the hooks 18, 19 is maintained.

After releasing the retaining thread 46, the rod 44 is taken to the release position, so that the circlet 48 is released from the rod 44. The practioner then pulls on the control portion 52 allowing the retaining thread 46 to escape from the metal lattice, by passing through the two meshes adjacent to the mesh carrying the clamp.

Thus, since the retaining device 30 of the clamp are made independent of the prosthesis 10, the retaining device 30 can be withdrawn by endoluminal means.

It will be understood that the prosthesis 10 is held effectively against the inner surface of the vessel by the presence of the clamps 16 which are maintained resiliently in the closed position under the action of the prosthesis 10. Furthermore, since the clamps 16 are closed at the same time as the prosthesis is put in place, installation of the prosthesis is relatively easy.

Moreover, the guiding of the hook 19 by the hook 18 stiffens the clamp 16 formed by the two hooks 18, 19. If one of the hooks 18, 19 is subjected to external stress, it is held by the other hook 18, 19 by the guiding member 20 so that they remain in the vicinity of each other. If the hooks 18, 19 are deformed around their respective fixing point 28, their relative position remains substantially unchanged and the function of the clamp 16 is maintained.

Obtaining the guiding member 20 by means of twisting the hook 18 on itself ensures that the manufacturing cost is low. Moreover, the hook 19 is moveable in the hook 18 along two orthogonal axes of rotation and at least one axis of translation. The stresses exerted between the hooks 18, 19 are thus minimized.

In a variant that has not been illustrated, the guiding member is carried by the lattice. The two hooks are then engaged in the guiding member. The guiding member consists for example of a rigid rod welded on the mesh carrying the clamp, the rod being extended by a ring forming the guiding member.

In a variant, the guiding member 20 is of any suitable known type, such as for example a ring integral with the hook 18.

Figure 11:
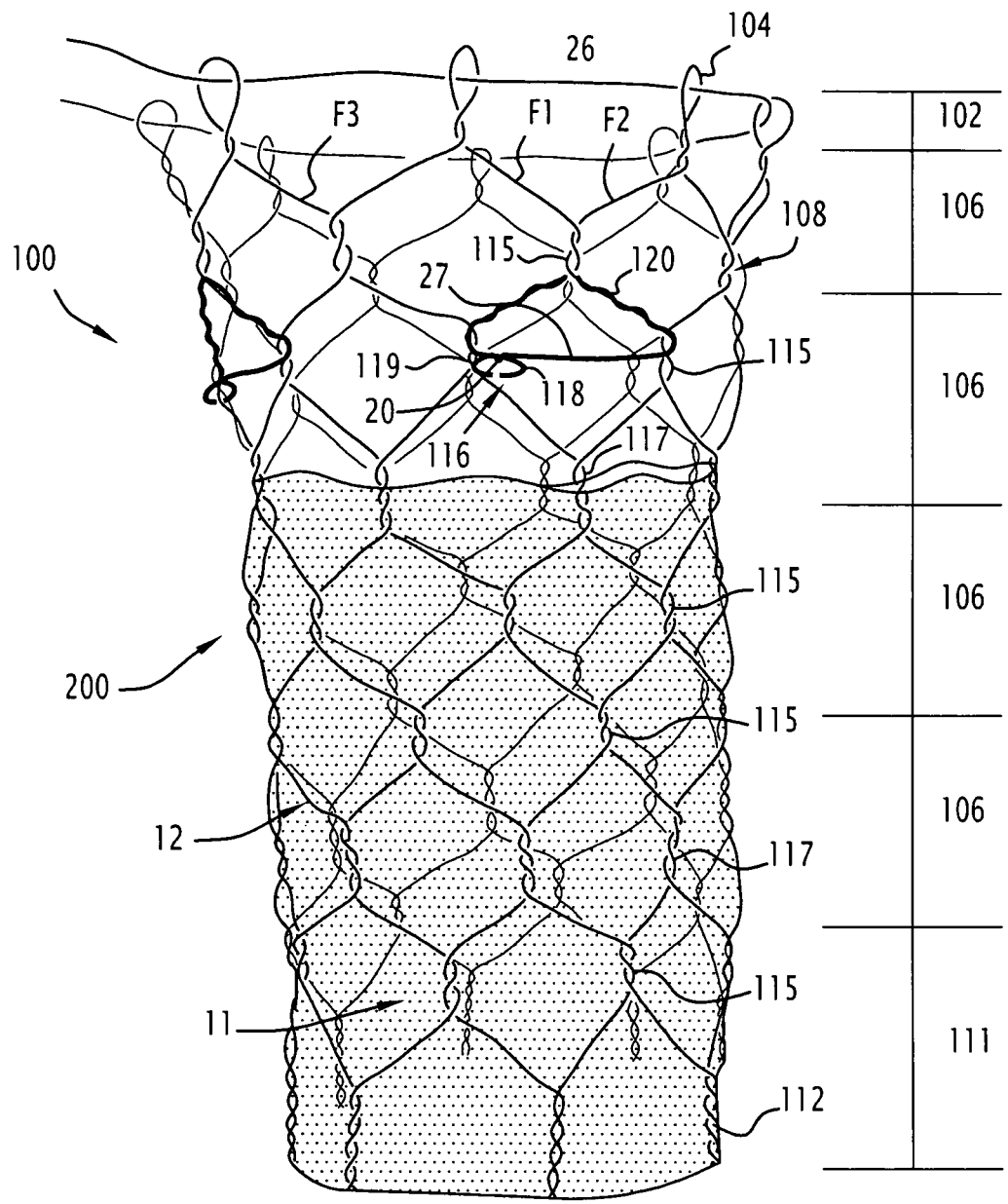
FIG. 11 is a perspective view in elevation of a variant embodiment of the prosthesis according to the invention.

Illustrated in FIG. 11 is a second embodiment of a prosthesis according to the invention.

The tubular body 11 of the vascular prosthesis 100 illustrated in FIG. 11 comprises a lattice 12 itself made up of eight resilient metal threads, such as the threads F1, F2 and F3, twisted together in a way that will be explained in detail below. These threads define, over the length of the lattice, several successive regions which are, from top to bottom in FIG. 11:

a first end region 102 with eight loops 104;
successive main regions 106 which each have peripheral crowns of twisted nodes 108; and
a second end region 111 with end twists 112.

In the case of the thread F1:
the loop 104 is formed by twisting the thread F1 on itself, by at least one half turn;
each node 108 is formed by twisting the thread F1 with an adjacent thread such as F2, F3 over one turn or more.

Thus, on either side of each so-called double-twisted node marked 115 where the thread is twisted over an even number of half turns in particular equal to two, each strand of the thread that forms the node extends in two directions parallel to each other and close to each other.

On the other hand, with regard to the so-called triple-twisted nodes 117 where the thread is twisted over an uneven number of half turns in particular equal to three, each thread emerges from it in two directions which between them form an angle considerably less than 180°, for example a right angle or an acute angle as illustrated, to form two adjacent sides of a mesh of the lattice.

As shown in FIG. 11, in the example illustrated, the thread F1 emerges from a twist 112 then forms successively a node 115, a node 117, a node 115, another node 115, a node 117, a node 115, another node 115, a loop 104, a node 115, another node 115, a node 117, a node 115, another node 115, a node 117, a node 115 and another twist 112.

In this embodiment, each clamp marked 116 is formed by a single metal thread 120, the running part of which is engaged and twisted round the threads delimiting the lattice, and the two free ends of which are curved outwards to form hooks 118, 119 similar to the hooks 18, 19 of the previous embodiment. The guiding hook 118 also comprises a guiding member 20 delimiting a guide passage 21 in which the guided hook 119 is engaged.

Figure 12:
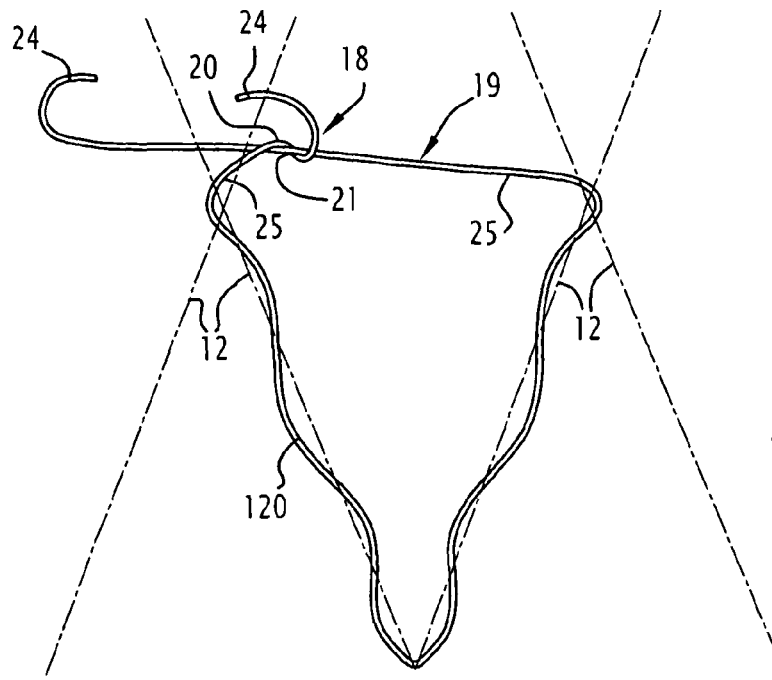
FIG. 12 is a view similar to FIG. 2 of the prosthesis of FIG. 11.
Figure 13:
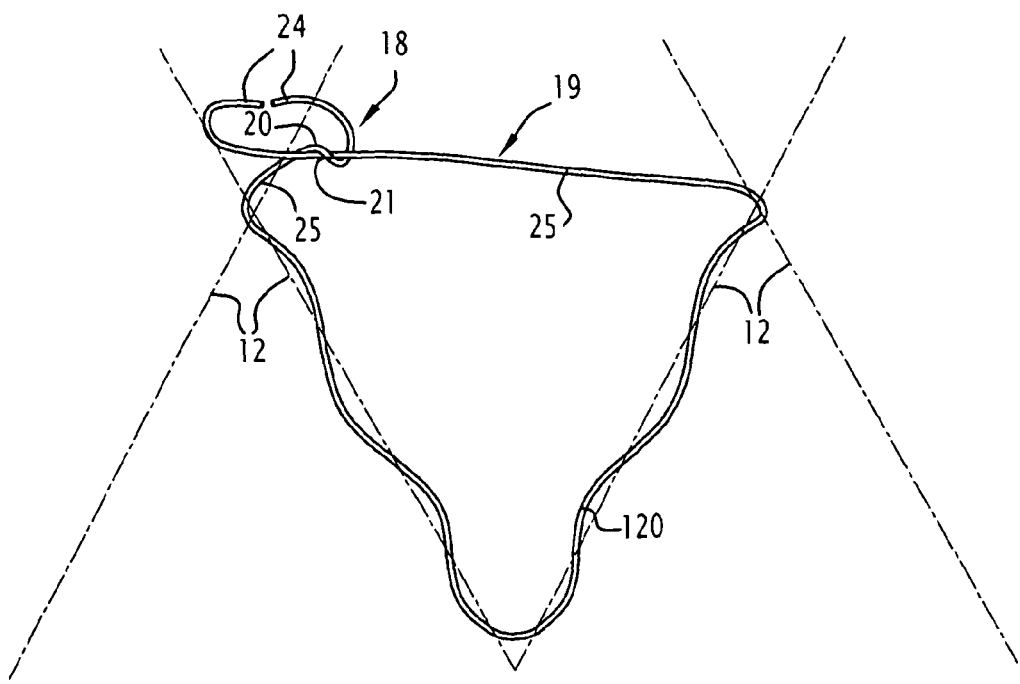
FIG. 13 is a similar view to FIG. 3 of the prosthesis of FIG. 11.

More precisely and as illustrated in FIGS. 11, 12 and 13, the thread 120 is twisted from a node 115 round two divergent and angularly offset strands. Each branch of the thread 120 is then twisted with the next twisted node and then extends transversely along a diameter of the mesh, to form the two arms 25 and the two endpieces 24 of the hooks 118, 119.

Thus, as in the previous embodiment, deformation of the mesh carrying the clamp 116 causes the clamp 116 to open or close, the two hooks 118, 119 at the curved end moving in relation to each other.

In the same way, the guiding member 20 ensures that fixing is reliable by maintaining the hooks 118, 119 facing each other after deployment of the prosthesis 100.

Figure 14:
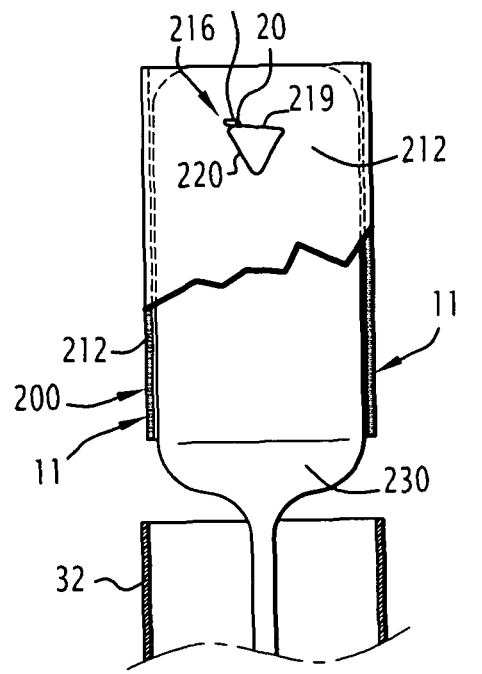
FIG. 14 is a side view in elevation of a prosthesis according to a third embodiment of the invention.

In a third embodiment illustrated in FIG. 14, the body 11 of the vascular prosthesis 200 is formed by a fabric tube 212 that can be deployed between a retracted state and an expanded state of large diameter. It is, for example, a Dacron™ fabric.

Two hooks 218, 219 similar to the hooks 118, 119 of the second embodiment are sewn on the tube 212. The hooks 218, 219 are formed by a single thread 220 in the form of a triangle, the hooks 218, 219 and the guiding member 20 being placed in the vicinity of the apex of the triangle. Deployment of the fabric 212 to its expanded state moves the two hooks 218, 219 between their spaced-apart position and their closer-together position, this movement being guided by the guiding member 20.

Unlike the previous two embodiments, the fabric 212 cannot be deployed spontaneously to its expanded state.

Initially, the fabric prosthesis 200 is held in its retracted state. In this state, the clamp 216 is open and the hooks 218, 219 are arranged spaced-apart from each other. The surface area delimited by the thread 220 in the form of a triangle is therefore minimal.

The prosthesis 200 is deployed by means of a small balloon 230 that can be inflated between a retracted state and an expanded state, and inserted in the fabric tube 212. The small balloon 230 is conveyed into the tube 212 by the delivery tube 32 it its retracted state and is then inflated.

Deployment of the fabric tube 212 causes the surface area delimited by the thread 220 to increase. The guided hook 219 then moves closer to the guiding hook 218 while being held close to the guiding hook by the guiding member 20.

By engaging radially in the blood vessel, the clamps 216 maintain the fabric 212 in its expanded state. Moreover, the two hooks 218, 219 axially engage the prosthesis 200, as in the two previous embodiments.

Unlike the two previous embodiments, the insertion member does not have a retaining device 30 for retaining the clamp 216 in its open position. Closure of the clamp 216 occurs as the fabric 212 is deployed.

Figure 15:
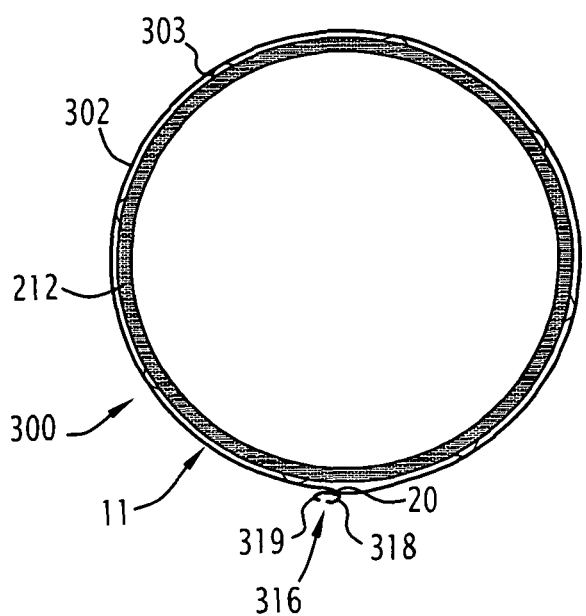
FIG. 15 is a view in section of a prosthesis according to a fourth embodiment of the invention.

In a fourth embodiment illustrated in FIG. 15, the body 11 of the prosthesis 300 is similar to that of the third embodiment. However, the prosthesis 300 also comprises a deformable ring 302 which encircles the fabric 212 and is sewn thereto by a thread 303. The ring 302 is therefore provided so as to deform with the fabric 212 between a retracted state in which it has a minimum diameter and an expanded state in which it has a maximum diameter.

Furthermore, the ring 302 carries at its ends the two hooks 318, 319 and the guiding member 20 and moves them between their spaced-apart position and their closer-together position during deformation thereof. The two hooks 318, 319 are for example similar to the hooks of the first embodiment, and have their ends 28 welded to the ring 302.

In a variant, the ring 302 is used with the prostheses 10, 100 of the first two embodiments.

The invention claimed is:

1. A radially deformable tubular prosthesis comprising:
a tubular body deformable between a retracted state of small diameter and an expanded state of larger diameter;
at least two hooks forming a clamp for engaging an outer tissue, said at least two hooks being carried by said tubular body and moveable between a spaced-apart position in which said clamp is open and a closer-together position in which said clamp is closed, said at least two hooks comprising a guiding hook and a guided hook; and
a guiding member formed on said guiding hook for guiding movement of said guided hook during movement of said at least two hooks between the spaced-apart position and the closer-together position, said guiding member being twisted around and engaging said guided hook so as to include at least two points of contact with said guided hook to guide translation of said guided hook along an axis of said guided hook;
wherein said at least two hooks and said guiding member are configured such that, when said at least two hooks draw closer, said guided hook slides in said guiding member, and
wherein each of said at least two hooks includes an end piece and an arm extending said end piece, and said guiding member is disposed at a predetermined distance from said end piece of said guiding hook.

2. The tubular prosthesis of claim 1, wherein each of said at least two hooks has a connection end connected to said tubular body, and said at least two hooks of said clamp are moveable relative to each other during deformation of said tubular body.

3. The tubular prosthesis of claim 1, further comprising a resilient ring encircling said tubular body, said ring being connected to said tubular body and being deformable with said tubular body between the retracted state and the expanded state, said ring carrying said at least two hooks so as to move said at least two hooks between the spaced-apart position and the closer-together position during deformation of said tubular body.

4. The tubular prosthesis of claim 1, wherein said tubular body includes a lattice deformable between the retracted state and the expanded state, said lattice comprising interlaced threads defining meshes shaped as deformable quadrilaterals, each of said at least two hooks being connected to said lattice at a corner of a respective one of said quadrilaterals.

5. The tubular prosthesis of claim 4, wherein each of said at least two hooks has a connection end fixed to said lattice.

6. The tubular prosthesis of claim 5, wherein each of said at least two hooks has an extension at said connection end comprising a strand twisted around said lattice.

7. The tubular prosthesis of claim 1, wherein said tubular body comprises a fabric deformable between the retracted state and the expanded state, said at least two hooks being fixed on said fabric such that deployment of said fabric moves said at least two hooks between the spaced-apart position and the closer-together position.

8. The tubular prosthesis of claim 1, wherein said guided hook contacts said guiding member over at least 180°.

9. The tubular prosthesis of claim 1, wherein the guiding member is twisted at least one turn around said guided hook.

10. The tubular prosthesis of claim 1, wherein the guiding member is twisted more than one turn around said guided hook.

11. A blood vessel treatment kit comprising:
a radially deformable tubular prosthesis including:
a tubular body deformable between a retracted state of small diameter and an expanded state of larger diameter;
at least two hooks forming a clamp for engaging an outer tissue, said at least two hooks being carried by said tubular body and moveable between a spaced-apart position in which said clamp is open and a closer-together position in which said clamp is closed, said at least two hooks comprising a guiding hook and a guided hook; and
a guiding member formed on said guiding hook for guiding movement of said guided hook during movement of said at least two hooks between the spaced-apart position and the closer-together position, said guiding member being twisted around and engaging said guided hook so as to include at least two points of contact with said guided hook to guide translation of said guided hook along an axis of said guided hook;
a retaining device for retaining said tubular body retracted in a region of said clamp; and
a delivery tube for delivering said tubular body to a desired location with respect to the outer tissue, said delivery tube configured to delimit a conduit for confinement of said prosthesis while said tubular body of said prosthesis is in the retracted state;
wherein said at least two hooks and said guiding member are configured such that, when said at least two hooks draw closer, said guided hook slides in said guiding member, and
wherein each of said at least two hooks includes an end piece and an arm extending said end piece, and said guiding member is disposed at a predetermined distance from said end piece of said guiding hook.

12. The kit of claim 11, wherein said conduit of said delivery tube comprises longitudinal channels for receiving said at least two hooks.

13. The kit of claim 11, wherein said retaining device includes:
a retaining rod extending through said delivery tube; and
a retaining thread having a circlet for engaging said retaining rod, a tightening loop portion for engaging said tubular body of said prosthesis, and a control portion connected to said tightening loop portion, said control portion extending through said delivery tube.

14. The kit of claim 11, wherein each of said at least two hooks has a connection end connected to said tubular body, and said at least two hooks of said clamp are moveable relative to each other during deformation of said tubular body.

15. The kit of claim 11, further comprising a resilient ring encircling said tubular body, said ring being connected to said tubular body and being deformable with said tubular body between the retracted state and the expanded state, said ring carrying said at least two hooks so as to move said at least two hooks between the spaced-apart position and the closer-together position during deformation of said tubular body.

16. The kit of claim 11, wherein said tubular body includes a lattice deformable between the retracted state and the expanded state, said lattice comprising interlaced threads defining meshes shaped as deformable quadrilaterals, each of said at least two hooks being connected to said lattice at a corner of a respective one of said quadrilaterals.

17. The kit of claim 11, wherein each of said at least two hooks has an extension at said connection end comprising a strand twisted around said lattice.

18. The kit of claim 11, wherein said tubular body comprises a fabric deformable between the retracted state and the expanded state, said at least two hooks being fixed on said fabric such that deployment of said fabric moves said at least two hooks between the spaced-apart position and the closer-together position.

19. A radially deformable tubular prosthesis comprising:
a tubular body deformable between a retracted state of small diameter and an expanded state of larger diameter;
at least two hooks forming a clamp for engaging an outer tissue, said at least two hooks being carried by said tubular body and moveable between a spaced-apart position in which said clamp is open and a closer-together position in which said clamp is closed, said at least two hooks comprising a guiding hook and a guided hook; and
a guiding member formed on said guiding hook for guiding movement of said guided hook during movement of said at least two hooks between the spaced-apart position and the closer-together position, said guiding member being twisted around and engaging said guided hook;
wherein said at least two hooks and said guiding member are configured such that, when said at least two hooks draw closer, said guided hook slides in said guiding member, and
wherein each of said at least two hooks includes an end piece and an arm extending said end piece, and each of said at least two hooks is connected to said tubular body at a respective anchoring point, a length of said arm of said guiding hook being smaller than a length of said arm of said guided hook so that said guiding member is proximate to the anchoring point of said guiding hook.

20. A radially deformable tubular prosthesis comprising:
a tubular body deformable between a retracted state of small diameter and an expanded state of larger diameter;
at least two hooks forming a clamp for engaging an outer tissue, said at least two hooks being carried by said tubular body and moveable between a spaced-apart position in which said clamp is open and a closer-together position in which said clamp is closed, said at least two hooks comprising a guiding hook and a guided hook; and
a guiding member formed on said guiding hook for guiding movement of said guided hook during movement of said at least two hooks between the spaced-apart position and the closer-together position;
wherein said at least two hooks and said guiding member are configured such that, when said at least two hooks draw closer, said guided hook slides in said guiding member, and
wherein each of said at least two hooks includes an end piece and an arm extending said end piece, and said guiding member is twisted around and engaging said guided hook so that guiding member is disposed in the vicinity of said end piece of said guiding hook.

* * * * *